(12) United States Patent
Corbeil et al.

(10) Patent No.: US 6,770,273 B1
(45) Date of Patent: Aug. 3, 2004

(54) VACCINE BASED ON ATTENUATED HAEMOPHILUS SOMNUS

(75) Inventors: Lynette B. Corbeil, San Diego, CA (US); Elizabeth J. Ziegler, San Diego, CA (US); Jerry D. Sanders, Fenton, MI (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/787,964

(22) PCT Filed: Sep. 24, 1999

(86) PCT No.: PCT/US99/22107

§ 371 (c)(1),
(2), (4) Date: Jun. 25, 2001

(87) PCT Pub. No.: WO00/18429

PCT Pub. Date: Apr. 6, 2000

Related U.S. Application Data

(60) Provisional application No. 60/101,760, filed on Sep. 25, 1998.

(51) Int. Cl.[7] .......................... A01N 63/00; A01N 65/00
(52) U.S. Cl. ..................... 424/93.1; 424/93.2; 424/93.4
(58) Field of Search .............................. 424/93.1, 93.2, 424/93.4

(56) References Cited

U.S. PATENT DOCUMENTS

| | | |
|---|---|---|
| 4,981,685 A | 1/1991 | Healey |
| 6,100,066 A | 8/2000 | Potter |

OTHER PUBLICATIONS

Briggs et al., "Characterization of a restriction endonuclease, Phat, from *Pasteurella haemolytica* serotype A1 and protection of heterologous DNA by a cloned Phal methyltransferase gene." b*Appl. Environ. Microbiol.* 60:2006–2010 (1994).
Cole et al., "Two linked genes for outer membrane proteins are absent in four non–disease strains of *Haemophilus somnus.*" *Mol. Microbiol.* 6:1895–1902 (1992).
Corbeil et al., "Antigenic specificity of convalescent serum from cattle with *Haemophilus somnus*–Induced experimental abortion.." *Infection and Immunity*, 55:1381–1386, (1987).
Corbeil et al., "Characterization of Immunodominant surface antigens of *Haemophilus somnus."* *Infect. Immun.* 59:4295–4301 (1991).
Corbeil et al., *Hemophilus somnus* Immunoglobulin binding proteins and surface fibrils. *Infect. Immun.* 65:4250–4257 (1997).

Corbeil et al., Serum susceptibility of *Haemophilus somnus* from bovine clinical cases and carriers. Journal of Clinical Microbiology, 22:192–198, (1985).
Ellis and Yong, "Systemic adverse reactions in young Simmental calves following administration of a combination vaccine." *Can. Vet.* 38:450–47, (1997).
Gogolewski et al., "Experimental *Haemophilus somnus* pneumonia in calves and immunoperoxidase localization of bacteria." *Vet. Pathol.,* 24:250–256, (1987).
Gogolewski et al., "Protective ability and specificity of convalescent serum from calves with *Haemophilus somnus* pneumonia." *Infect. Immun.* 55:1403–1411, (1987).
Gogolewski et al., "Protective ability of antibodies against 78– and 40–Kilodalton outer membrane antigens of *Haemophilus somnus.*" Infection and Immunity 56:2307–2316, (1988).
Gogolewski et al., "Pulmonary persistence of *Haemophilus somnus* in the presence of specific antibody," *J. Clin. Microbiol.* 27:1767–1774, (1988).
Gu et al., "Quantitation and biological properties of released and cell–bound lipooligosaccharides from nontypeable *Haemophilus influenzae."* *Infect. Immun.* 63:4115–4220, (1995).
Harris and Janzen, "The *Haemophilus somnus* disease complex (Hemophilosis): A review." *Can. Vet. J. 30*:816–822, (1989).
Inzana et al., "Phenotypic phase variation in *Haemophilus somnus* lipooligosaccharide during bovine pneumonia and after in vitro passage." *Infect. Immun. 60*:2943–2951, (1992).
Van Donkersgoed et al., "The effect of a combined *Pasteurella haemolytica* and *Haemophilus somnus* vaccine and a modified–live bovine respiratory syncytial virus vaccine against enzootic pneumonia in young beef calves." *Can. Vet. J. 35*:239–241, (1994).
Widders et al., "Experimental abortion and the systemic immune response to *Haemophilus somnus* in cattle." *Infection and Immunity, 54*:555–560, (1986).
Yang et al., "Apoptosis: A possible tactic of *Haemophilus somnus* for evasion of killing by bovine neutrophils?" *Microbiol Pathogenesis, 24*:351–159, (1998).

*Primary Examiner*—Mark Navarro
(74) *Attorney, Agent, or Firm*—Foley & Lardner

(57) ABSTRACT

The present invention provides a method for protecting cattle from diseases such as septicemia, pneumonia or abortion by immunizing them with an *H. somnus* vaccine. Provided are natural isolates of *H. somnus* strains that have one or more important features of such vaccine, including, sensitivity to killing in complement-containing bovine serum, lack of expression of immunoglobulin binding proteins, expression of protective antigens and a reduction in the release of endotoxin during growth. Vaccines using *H. somnus* having these and other features also can be prepared from natural isolates of asymptomatic carriers or from pathogenic organisms by recombinant DNA techniques.

11 Claims, 1 Drawing Sheet

VACCINE BASED ON ATTENUATED HAEMOPHILUS SOMNUS

Figure 1:

This application is the national phase of PCT/US99/22107, filed Sep. 24, 1999, which claims benefit of US Provisional Application 60/101,760, filed Sep. 25, 1998.

This research was supported by funding from the United States Department of Agriculture. Accordingly, the United States may have rights in the invention.

BACKGROUND OF THE INVENTION

The present invention relates generally to the prevention of diseases of cattle and, more specifically, to immunizing against such diseases by vaccination.

Bovine respiratory disease (BRD), bovine septicemia and bovine reproductive failure (BRF) result in great economic loss to the cattle industry. The primary bacterial pathogens implicated in BRD are *Pasteurella haemolytica, P. multocida* and *Haemophilus somnus*. *H. somnus* also causes bovine reproductive failure (BRF) and septicemia.

Current vaccines for *H. somnus* consist mainly of killed bacteria (bacterins) or bacterial extracts. Although there is evidence for protection in some controlled laboratory or animal challenge studies, efficacy in field studies is generally lacking. In some cases the vaccines cause such adverse side effects that their use is very limited. In other cases, little protection is seen. Thus, there is a need to develop improved vaccines to protect cattle from *H. somnus* mediated diseases. Such vaccines should contain key protective antigens that elicit appropriate antibody and cell-mediated immune responses. In addition, such vaccines should lack factors that cause adverse reactions and enable pathogens to evade immune recognition or effector mechanisms.

SUMMARY OF THE INVENTION

Accordingly, it is an object of the present invention to provide an effective and safe *H. somnus* vaccine for protection against BRD, BRF, septicemia and related disorders.

To accomplish these and other objectives, there has been provided, in accordance with one aspect of the present invention, a method for vaccinating cattle against diseases mediated by infection, comprising administering an effective amount of an *H. somnus* vaccine, wherein the *H. somnus* is susceptible to killing by bovine complement-containing serum.

According to another embodiment of the present invention, the *H. somnus* is live.

According to another embodiment of the present invention, the *H. somnus* is killed.

According to yet another embodiment of the present invention, the *H. somnus* lacks the expression of one or more immunoglobulin binding proteins present in virulent *H. somnus*. In a further embodiment, the lack of expression of one or more immunoglobulin binding proteins is achieved by the step of genetically engineering *H. somnus* to delete genes encoding the immunoglobulin binding proteins.

According to still yet another embodiment of the present invention, the *H. somnus* expresses a protective antigen. In a further embodiment, the protective antigen is a 40 kDa outermembrane protein.

According to another embodiment of the present invention, the *H. somnus* releases reduced amounts of endotoxin during growth as compared to virulent *H. somnus*.

According to yet another embodiment of the present invention, the *H. somnus* is selected from the group consisting of PTA-600, PTA-601, PTA-602 and PTA-603, all on deposit with the American Type Culture Collection.

In accordance with another aspect of the present invention, a method is provided for vaccinating cattle against diseases mediated by infection, comprising administering an effective amount of an *H. somnus* vaccine, wherein the *H. somnus* releases reduced amounts of endotoxin as compared to virulent *H. somnus*.

According to another embodiment of the present invention, the *H. somnus* is live.

According to another embodiment of the present invention, the *H. somnus* is killed.

According to yet another embodiment of the present invention, the *H. somnus* is sensitive to killing by complement-containing bovine serum.

According to still yet another embodiment of the present invention, the *H. somnus* lacks the expression of one or more immunoglobulin binding proteins present in virulent *H. somnus*. In a further embodiment, the lack of expression of one or more immunoglobulin binding proteins is achieved by the step of genetically engineering *H. somnus* to delete genes encoding the immunoglobulin binding proteins.

According to another embodiment of the present invention, the *H. somnus* expresses a protective antigen. In a further embodiment, the protective antigen is a 40 kDa outermembrane protein.

According to yet another embodiment of the present invention, the *H. somnus* is selected from the group consisting of PTA-600, PTA-601, PTA-602 and PTA-603, all on deposit with the American Type Culture Collection.

In further embodiments of the present invention, the vaccines described above use an *H. somnus* genetically engineered to express one or more protective antigens. In further embodiments, the protective antigens are from bacterial pathogens other than *H. somnus*.

Other objects, features and advantages of the present invention will become apparent from the following detailed description.

BRIEF DESCRIPTION OF DRAWINGS

FIG. 1 is an SDS-polyacrylamide gel showing lipooligosaccharide (LOS), also known as endotoxin, associated with cells or released into media during growth of a virulent *H. somnus strain* (2336) or avirulent *H. somnus* natural isolates (129Pt and 1P). Organisms grown in brain heart infusion broth containing 0.1% Tris base and 0.01% thiamine monophosphate were shaken at 37° C. At 24 hours, cultures were adjusted to 75% light transmission (610 nm) and a cell pellet (CP) was separated from the supernatant (S) by centrifugation. CP and S were digested with RNAse followed by proteinase K. After electrophoresis, the gel was silver-stained. Virtually no released LOS could be detected in the S of the avirulent *H. somnus* natural isolates, while the amount of LOS in the CP of both natural isolates and virulent strain of *H. somnus* was similar.

DETAILED DESCRIPTION OF THE INVENTION

The present invention provides methods for protecting cattle against diseases including, for example, bovine respiratory disease (BRD), bovine septicemia and bovine reproductive failure (BRF), thrombotic meningoencephalitis, arthritis, myocarditis (Gogolewski et al., Infect. Immun. 56:2307–2316 (1989); Gogolewski et al., *J. Clin. Microbiol.* 27:1767–1774 (1988); Harris et al., *Can.*

*Vet. J.* 30:816–822 (1989) and Van Donkersgoed et al., *Can. Vet. J.* 35:239–241 (1994)) by immunizing the cattle with an *H. somnus* vaccine. For this purpose, the present invention provides *H. somnus* strains 1P, 129Pt, 130Pfl and 133P, isolated from prepuce of normal bulls and deposited with the American Type Culture Collection as PTA-600, PTA-601, PTA-602 and PTA-603, respectively, on Sep. 1, 1999.

These "natural" isolates of *H. somnus* are particularly suitable for use in the vaccine method of the present invention because they have several important features. These include, for example, sensitivity to killing in complement-containing bovine serum, lack of expression of immunoglobulin binding proteins, expression of protective antigens and a reduction in the release of endotoxin during growth. The present invention is not limited to such natural isolates. A useful vaccine can include *H. somnus* natural isolates that have less than all the above listed features as well as pathogenic organisms modified so as to share one or more of the unique features associated with the natural isolates. *H. somnus* organisms with such features can be obtained by isolation from natural sources or from diseased tissue. In addition, as discussed further below, useful features for a vaccine can be introduced into by using recombinant DNA techniques to modify *H. somnus*.

One feature of an effective vaccine comprising *H. somnus* is sensitivity to killing in complement-containing bovine serum. *H. somnus* organisms with this feature can be isolated from preputial sites of clinically normal cattle (i.e., asymptomatic carriers) by standard methods (Corbeil et al., *J. Clin. Microbiol.* 22:192–198 (1985)). Such organisms are considered "serum sensitive." Alternatively, the feature of serum sensitivity can be introduced into wildtype or virulent organisms by deleting genes encoding for immunoglobulin binding proteins. Gene deletion methods useful for this purpose, such as homologous recombination, are well known in the art (see Example 2(*d*)). Thus, the present methods include use of a vaccine comprising *H. somnus* that is sensitive to killing in complement-containing bovine serum.

The present invention also includes methods of immunization using a vaccine comprising *H. somnus* lacking genes for a family of proteins associated with serum resistance. These genes encode immunoglobulin (Ig) binding proteins such as an approximately 120 kDa group of extracellular fibril associated Ig binding proteins and a 76 kDa Ig binding protein present in the outer membrane (Corbeil et al., *Infect. Immun.* 65:4250–4257 (1997)). These Ig binding proteins bind the Fc portion of bovine IgG2. Virulent strains of *H. somnus* bind IgG2 to the surface and it is believed such strains evade immune recognition by the host because critical protective antigens expressed by the pathogen are masked by the bound bovine IgG2. Thus, *H. somnus* organisms that express decreased amounts of Ig binding proteins because of gene deletion, mutation or by other mechanisms are useful herein for vaccinating cattle. *H. somnus* strains 1P, 129Pt, 130Pfl and 133P (deposited as PTA-600, PTA-601, PTA-602 and PTA-603, with the ATCC) are missing 13.4 kb of DNA, which encodes the 120 kDa group and 76 kDa Ig binding proteins discussed above.

Another feature of *H. somnus* rendering it useful as a vaccine is the expression of a 40 kDa (p40) protective surface antigen (Corbeil et al., *Infect. Immun.* 59:4295–4301 (1991)). Monospecific bovine IgG1 and IgG2 antibody stimulated against such p40 antigen passively protects calves against *H. somnus* induced pneumonia (Gogolewski et al., *Infect. Immun.* 56:2301–2316 (1988)). The antigen is expressed on the surface of *H. somnus* (id.) and conserved in all strains tested (id.). Furthermore, this p40 antigen cross-reacts strongly with surface exposed antigens of other organisms, including, *P. haemolytica* and *P. multocida* (id.). Thus, expression of the p40 surface antigen in *H. somnus* of the vaccine also can protect cattle against infection by other organisms.

Another important feature of a useful vaccine based on gram negative organisms is the avoidance of serious complications often associated with endotoxin from the vaccine. *H. somnus* produces a lipooligosaccharide (LOS) which has endotoxic activity similar to that of *E. coli* J5 LOS (Inzana et al., *Infect. Immun.* 56:2830–2837 (1988)) and pathogenic *H. somnus* organisms that have been previously used as a vaccine are known to be associated with serious inflammation or endotoxic shock (Ellis et al., *Can. Vet.* 38:450–47 (1997)). Thus, a vaccine that sheds less LOS should have reduced toxicity.

In this regard, the present invention provides *H. somnus* organisms that release substantially reduced amounts of endotoxin during growth. The amount of LOS released by *H. somnus* in the vaccine of the present methods is preferably less than that released by virulent strains, more preferably less than 10% of that released by virulent strains and most preferably less than 1% of that released by virulent strains. For example, virulent strain 2336 releases almost 0.04 mg/ml (40 $\mu$g/ml) LOS in supernatant at 24 hours of culture (Example 1). Thus, nonvirulent *H. somnus* strains useful as a vaccine of the invention preferably release less than 40 $\mu$g/ml LOS, more preferably less than 4 $\mu$g/ml LOS, and most preferably less than 0.4 $\mu$g/ml of LOS into the culture supernatant during about 24 hours of culture, which includes an exponential growth phase followed by a stationary growth phase.

*H. somnus* strains 1P, 129Pt, 130Pfl and 133P (deposited as PTA-600, PTA-601, PTA-602 and PTA-603, with the ATCC) release much reduced levels of LOS during log and stationary phases of growth, although these natural isolates have similar amounts of LOS associated with the cell pellet as does the virulent *H. somnus* (e.g. strain 2336, 649 and 8025). Since free endotoxin of Haemophilus Influenzae was shown to be more toxic than cell bound endotoxin (Gu et al., *Infect. Immun.* 63:4115–4220 (1995)), a significant reduction in released endotoxin is likely to be important in preventing tissue reactions at the inoculation site and systemic reactions to vaccination that occur frequently with virulent *H. somnus* bacterins.

LOS with complete core sugars undergoes antigenic variation resulting in evasion of host response (Inzana et al., *Infect. Immun.* 60:2943–2951 (1992)). LOS from virulent serum-resistant strains of *H. somnus* undergoes antigenic variation in vivo and in vitro, but LOS from some serum-sensitive preputial isolates does not undergo antigenic variation, at least in vitro (id.). Thus, the LOS that remains associated with the organism in serum-sensitive *H. somnus* isolates used in the vaccines of the present invention have the added advantage of providing a more stable antigenic target than LOS associated with virulent strains.

The mechanism by which natural isolates from asymptomatic carriers release less LOS is unknown. Nevertheless, *H. somnus* organisms with this feature can be found by screening natural isolates from healthy cattle. Such organisms can be identified by analyzing culture medium of growing organisms for LOS as described in Example 1 using the silver staining method Tsai-Frasch or by detection of LOS using monoclonal antibody prepared essentially as described in Inzana et al., *Infect. Immun.* 56:2830–2837 (1988)). In addition, a reduction in released endotoxin can be shown in an animal model of endotoxic shock in which live organisms (generally about $10^6$ to $10^9$ cells) are injected intraperitoneally into mice and endotoxic shock determined by lethality or moribundity.

The *H. somnus* vaccine is preferably administered as an attenuated live vaccine. With live vaccines, the amount of organism in a useful dose is generally less than for killed vaccines. Consequently, live vaccines have the advantage of presenting less endotoxin to the recipient and avoiding some of the associated toxicity, including local tissue reactions and occasionally death. Although administration of a live *H. somnus* vaccine raises concerns of septicemia following multiplication and dissemination, live *H. somnus* that are sensitive to complement-containing bovine serum do not raise such concerns because the plasma complement of blood should kill these organisms when they reach the blood stream. Organisms lacking genes associated with serum complement resistance and lacking expression of one or more Ig binding proteins are particularly suited for use as a live attenuated vaccine because the encoding DNA is missing from such organisms.

However, administration of vaccines wherein the *H. somnus* organisms are killed also is contemplated herein. The organisms can be killed by methods well known in the art including, for example, by chemical methods such as formalin or by physical inactivation methods such as by heat.

A live or killed *H. somnus* vaccine can be administered systemically, or by any other suitable route including, for example, intradermally, intramuscularly, or subcutaneously. In particular, the vaccine can be administered to a mucosal surface such as the nasal, upper respiratory tract or vaginal surface as these surfaces are naturally colonized by *H. somnus*. The vaccine can be administered in a conventional active immunization scheme: single or repeated administration in a manner compatible with the dosage formulation, and in such amount as will be prophylactically effective, i.e. the amount of immunizing *H. somnus* antigen that induces immunity in cattle against challenge by virulent *H. somnus*. Immunity is defined as the induction of a significant level of protection in a population of cattle after vaccination compared to an non-vaccinated group.

An attenuated live vaccine which is serum-sensitive is preferably administered by inoculation subcutaneously or on a mucosal surface. This is desirable because the administered organisms are initially viable and can replicate at such sites until they are killed by complement that accumulates during inflammation. Because serum-sensitive strains are killed by complement, they would not survive in complement-containing tissue such as an inflammatory site or in the blood. The ability of an attenuated live vaccine to at least replicate for a short time in the host is generally associated with improved immunity over that obtained with a killed vaccine.

Administration of the vaccine via a mucosal route also has the advantage of eliciting protective IgA as well as IgG antibody. Such antibodies have been elicited by respiratory inoculation of virulent *H. somnus*, resulting in protection against challenge with 10× the original infective dose (Gogolewski et al., *J. Clin. Microbiol.* 27:1767–1774 (1989)).

Vaccine formulations will contain an effective amount of the active ingredient. i.e., *H. somnus* or a preparation thereof, in a pharmaceutically acceptable vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal considered for vaccination. The quantity also depends upon the capacity of the animal's immune system to synthesize antibodies, and the degree of protection desired. Effective dosages can be readily established by one of ordinary skill in the art through routine trials establishing dose response curves.

Vehicles for the vaccine include, for example, aqueous saline, aqueous buffer, or other known substances. The vehicle also can include other constituents known to increase the activity and/or the shelf life. These constituents may be salts, pH buffers, stabilizers (such as skimmed milk or casein hydrolysate), emulsifiers, adjuvants to improve the immune response (e.g. oils, muramyl dipeptide, aluminum hydroxide, saponin, polyanions and amphipatic substances) and preservatives, (e.g. chlorobutanol and benzalkonium chloride).

The vaccine containing *H. somnus* can be tested in vivo for efficacy in animal models or experimental *H. somnus*-induced disease in the natural host. Such models include pneumonia, abortion and septicemia.

Immunity to *H. somnus*-induced pneumonia in cattle can be evaluated in models reported previously (Gogolewski et al., *Infect. Immun.* 55:1403–1411 (1987). Gogolewski et al., *Vet. Path.* 24:250–256 (1987)). In this approach, cattle immunized the vaccine administered as described above are tested for efficacy by administering small doses of *H. somnus* strain 2336 ($10^6$–$10^8$CFU) in 2 ml intrabronchially by flexible fiber optic scope or nasotracheal tube to 6–12 week old calves. Transtracheal inoculation of the vaccine also can be used in this model.

Immunity to experimental *H. somnus*-induced abortion can be evaluated in models reported previously (Widders et al., *Infect. Immun.*, 54:555–560 (1986). Corbeil et al., *Infect. Immun.* 55:1381–1386 (1987)). In this approach, pregnant cattle previously immunized with the vaccine administered as described above are tested for efficacy by administering large doses ($4 \times 10^{10}$ CFU) of virulent *H. somnus* (e.g., strain 649) either intravenously or intrabronchially.

Immunity to experimental *H. somnus*-induced septicemia can be evaluated in mice or cattle immunized with vaccine administered as discussed above wherein septicemia is induced by intravenous or intraperitoneal inoculation of virulent organisms in cattle or mice, respectively.

*H. somnus* organisms used in the vaccine of the present invention can be genetically modified so as to acquire any of the features described above. For example, *H. somnus* organisms can be modified to express the 40 kDa *H. somnus* surface antigen associated with vaccine protection if the organisms do not express such antigen. Alternatively, an additional gene for the 40 kDa *H. somnus* antigen can be genetically inserted into the organism to enhance the resulting immune response and increase protection. Such a vaccine can induce antibodies against cross reactive surface antigens of *H. somnus*, *P. multocida* and *P. haemolytica* (Corbeil et al., *Infect. Immun.* 59:4295–4301 (1991)). In addition, other *H. somnus* antigen-encoding genes can be genetically inserted into *H. somnus*. Such antigens include, for example, p76, p78, p60, p39 and the like, which provide protection against *H. somnus*-induced disease and some minor cross protection against other Pasteurellaceae-induced disease.

The present invention also provides methods of protecting cattle by immunizing with a recombinant multivalent *H. somnus* vaccine that results in protective immunity against disease causing agents other than *H. somnus*. Genes for antigens of other pathogens causing syndromes in cattle also can be used to construct a recombinant multivalent vaccine based on *H. somnus* (e.g., bovine respiratory disease). By this approach, protection that builds upon the cross-protectivity of the *H. somnus* antigens is achieved by using recombinant techniques to express protective antigens from *H. somnus*-related disease-causing organisms such as from other Pasteurellaceae. For example, the leukotoxin genes of *P. haemolytica* can be expressed by recombinant methods in *H. somnus* organisms of the vaccine to provide both specific anti-leukotoxin antigen and cross-protective anti-40 kDa outermembrane antigen mediated-protection. Therefore, the vaccine would protect against both *H. somnus* and *P. haemolytica*. Genes for other protective antigens of the Pasteurellaceae family of organisms also may be expressed in *H. somnus* organisms to provide a vaccine broadly protective for a group of infections (e.g., bovine respiratory disease caused by *P. haemolytica, P. multocida* and *H. somnus*).

To protect against bovine reproductive failure, genes of organisms causing abortion or infertility such as protective surface antigens of *Leptospira interrogans, Neospora caninum, Tritrichomonas foetus*, and/or *Campylobacter fetus subsp, venerealis*, can be expressed by genetically engineering the *H. somnus* strains discussed above. Other combinations could be used to protect against agents causing septicemia, arthritis, and/or meningenocephalitis.

A multivalent *H. somnus* vaccine also can be engineered to provide protection against bacterial and viral diseases of cattle. For example, protective antigens for viral BRD or BRF diseases of cattle can be expressed in the *H. somnus* organisms of the vaccine. Such vaccines can comprise *H. somnus* expressing protective vial antigens alone or in combination with other protective bacterial antigens.

Multivalent recombinant vaccines for pneumonia and septicemia can be administered to animals at an appropriate age while a multivalent recombinant vaccine for reproductive failure can be administered to animals at an appropriate time before breeding. Methods for introducing genes into bacteria or deleting/inactivating host genes are well known in the art. Example 2 describes cloning vectors and recombinant DNA strategies for genetically engineering *H. somnus* to express foreign genes and to delete host genes.

EXAMPLES

Example 1

Analysis of *H. somnus* Strains for Proteins and Endotoxins

This example describes methods for growing *H. somnus* and measuring protein and endotoxin associated with cells and released into the supernatant.

*H. somnus* organisms were grown in brain heart infusion broth containing 0.1% Tris base and 0.01% thiamine monophosphate by vigorous shaking at 37° C. At various times, a sample of culture was removed and adjusted to 75% light transmission (610 nm) and the cells (CP) were separated from the supernatant (S) by centrifugation. Endotoxin (LOS) and protein antigens (PA) associated with the cell pellet and the supernatant were analyzed by Sodium dodecyl sulfate-polyacrylamide gel electrophoresis (SDS-PAGE) and Western blotting, respectively.

For LOS detection, cell pellet (CP) and supernatant (S) were digested with RNAse followed by proteinase K, samples were run on SDS-PAGE (15% polyacrylamide and 3% urea) and LOS was visualized in the gel by the Tsai-Frasch silver staining method (Tsai et al., *Ann. Biochem.* 119:115–119 (1982)). Quantitation of LOS in the SDS gels was accomplished using LOS standards obtained by extracting LOS from *H. somnus* virulent isolates using a modification of the hot phenol-water method of Westphal (Westphal and Jann. Academic, Press, New York p83–91 (1965)). Standards and experimental LOS samples were evaluated by densitometry using the NIH Image Program, v 1.60.

Proteins were detected by Western blotting essentially as described in Gogolewski et al., *Infect. Immun.* 55:1403–1411 (1987)). Samples of CP and S, solubilized in SDS-PAGE sample buffer, were run on standard Laemmli SDS-PAGE, electrotransferred to nitrocellulose paper and then immunoblotted using convalescent bovine serum (Gogolewski et al., *Infect. Immun.* 55:1403–1411 (1987)) followed by anti-bovine Ig antibody alkaline phosphatase conjugate.

For cell pellets from both virulent and natural isolates, the amount of LOS or PA detected remained constant over time. The release of PA was minimal, increasing slightly over time. However, for virulent strains 2336 and 640, free LOS doubled from early (5 to 6 hrs) to late log phase (10 hrs), reaching about 0.04 mg/ml of S, a value about half that of LOS in the cell pellet. Free LOS in the supernatant doubled again in amount at 24 hrs (the stationary phase).

For the natural isolates from asymptomatic carriers, 129Pt and 1P, S from stationary cultures at 24 hours contained almost no LOS detectable by silver staining of SDS-PAGE gels, although the amount in CP was about the same as for the virulent strains.

Example 2

Preparation of Genetically Engineered *H. somnus* Vaccine

This example describes recombinant DNA methods for genetically engineering *H. somnus* organisms to express foreign genes or delete selected host genes.

a) Modification and Subcloning of *H. somnus* Genes:

To facilitate subcloning into pLS88Bgl II, the recombinant plasmid pHS139 (Cole et al., *Mol. Microbiol.* 6:1895–1902 (1992), Cole et al., *J. Gen. Microbiol.* 139:2135–2143 (1993)), which expresses the p76 protein was modified in the following manner. pHS139 was digested with Pvu II and the 5.5 kb fragment which contained the insert and flanking vector DNA was isolated. Cla I linkers were ligated to the 5.5 kb fragment. The ligation was digested with Cla I and BamH I and the resulting 5.2 kb fragment was isolated. The plasmid pLS88δBgl II was digested with Cla I and Bgl II and the 4.6 kb fragment was isolated. The 5.2 kb BamH I/Cla I fragment containing the p76 gene was ligated to the 4.6 kb Cla I/Bgl II vector fragment of pLS88δBgl II. The ligation was electroporated into *E. coli* strain DH5α with selection for streptomycin resistance. Plasmid DNA was isolated from selected clones and the presence of the 5.2 kb insert within the 4.6 kb vector was determined by restriction analysis. The recombinant plasmid was designated pJDS160. Subsequently the plasmid pLS88Poly has been utilized for subcloning the gene of the p120 Ig binding protein family (pJDS161). Additionally, the kanamycin gene flanked by BamH I sites has been used to engineer a construct designed to inactivate the gene encoding the p120 Ig binding protein family (pJDS162).

b) In Vivo Methylation of Recombinant Plasmids:

Differences in restriction modification can impact the efficiency at which DNA from one bacterial organism is taken up by another. Transformation of recombinant plasmids from *E. coli* into *H. influenzae* suggest this fact and restriction modification was reported as a problem with genetic exchange in *P. haemolytica* (Briggs et al., *Appl. Environ. Microbiol.* 60:2006–2010 (1994)). These observations indicate that prior methylation of recombinant plasmid constructs might overcome difficulties with electroporation of plasmid DNA into *H. somnus*.

The restriction modification system of *H. somnus* has not been characterized and while commercially available methylases might protect one or more sites, a much more broad scale protection is desirable. The restriction modification system (including methylation sites) has been characterized for the related species *H. influenzae* and the genetics of this species has been thoroughly investigated. Furthermore, *H. influenzae* genes cloned in *E. coli* could be transferred back into *H. influenzae* although at a reduced efficiency as compared to *H. influenzae* to *H. influenzae* gene transfer. Thus, recombinant vectors containing *H. somnus* genes could be introduced into *H. influenzae* for methylation and then removed and used for transformation of *H. somnus*.

Analysis of the nucleotide sequence of the insert from pHS139 shows 13 potential sites for four *H. influenzae* restriction enzymes (with concurrent methylation sites). *H. influenzae* Rd strain DB117, a recombinant-deficient (rec-1) cloning strain (plasmids introduced into the strain are unable to undergo recombination with the chromosome), was selected as a methylation source. All recombinant plasmids were first electroporated into this strain. Recombinant plasmids were isolated after methylation and their identity was confirmed by restriction analysis. While this system was applied to methylation of *H. somnus* genes previously cloned into *E. coli*, this system should be applicable to methylation of cloned genes from varied sources.

c) Conditions for Electroporation of Recombinant Plasmids Into *H. somnus:*

Recombinant plasmids were electroporated into *H. somnus* under optimized conditions. Strains were grown in brain heart infusion broth supplemented with 0.01% thiamine monophosphate and 10% Levinthal Base to an optical density, $OD_{600}$ of 0.600 (+/−0.100). Cells were chilled on ice for 30 minutes, and then harvested by centrifugation at 4300×g for 5 minutes at 4° C. *H. somnus* cell pellets were washed twice in 272 mM sucrose buffer with centrifugation for 20 minutes at 4,300×g for each wash. After the final wash, the cell pellet was suspended in cold 272 mM sucrose buffer to yield a 100 fold increase over the original cell concentration. Cell volumes of 39 μl and DNA concentrations of about 300 ng were used for electroporation.

Electroporation of *H. somnus* was at a field strength of 16.0 Kv/cm with a cuvette gap of 1 mm and a resistance of 186 ohms. Reactions after pulsing were diluted to 1 ml with media, chilled on ice for 10 minutes, incubated at 37° C. for 1 hour, and plated for selection. Plasmid DNA was isolated from selected clones and the identity was confirmed by restriction digests.

Expression of the introduced genes was demonstrated by Western blot analysis of lysates of selected clones. In addition to the electroporation of pJDS160 and consequent expression of the p76 protein in *H. somnus* strain 129Pt, constructs pJDS161 and pJDS162 also have been electroporated into 129Pt. Although conditions for electroporation have been established for *H. somnus* strain 129Pt, conditions may need to be varied for different strains.

d) Inactivation of *H. somnus* Genes by Deletion/Insertion:

The general approach to gene inactivation involves introduction of the specific gene with a significant portion of the encoding region deleted and replaced with a selectable marker (e.g., kanamycin resistance gene from pLS88PolyKan utilizing flanking multiple cloning sites). Inactivation of the specific chromosomal gene relies on homologous recombination with common DNA flanking the antibiotic resistance marker. After introduction of the modified gene into the target strain by electroporation, homologous recombination with allelic exchange can occur in two forms (i) as fragment with minimal flanking vector DNA, or (ii) as an insert within a suicide vector. With either approach, the introduced genetic elements would not be able to replicate independently in the target strain.

The multiple cloning sites flanking the kanamycin gene present in pLS88PolyKan offers the potential to inactivate specific genes of *H. somnus* to produce avirulent strains or to produce inactivated, selectable genes from different pathogens for recombinant vaccine construction. The use of a fragment for homologous recombination may be more specific for allelic exchange than the suicide vector as shown previously for *H. ducreyi* (Hansen et al., *J. Bact.* 174:5442–5449 (1992)).

The p120 gene encoding an Ig binding protein can be inactivated using this system. The subclone, pHS119, was used as a basis for deletion/inactivation. The plasmid pHS119 contains the C-terminal region of the gene encoding the p120 protein family. The Hind III insert of pHS119 was ligated into the Hind III site of pLS88. The kanamycin gene from pLS88PolyKan with flanking BamH I sites was ligated into the Bgl II site of the insert creating pJDS162.

To inactivate the gene encoding the p120 Ig binding protein, the insert with minimal flanking vector DNA is excised from pJDS162, isolated, and electroporated into an *H. somnus* strain expressing the high molecular weight (HMW) Ig binding proteins. Inactivation of the gene encoding the p120 protein occurs through homologous recombination with selection for kanamycin resistance as an indication of allelic exchange. Kanamycin resistant clones are screened for expression of HMW Ig binding proteins by Western blotting. Integration of the kanamycin resistance gene within the chromosomal gene encoding the p120 protein is demonstrated by Southern blotting.

The examples set forth above are provided to give those of ordinary skill in the art a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for vaccinating cattle against *Haemophilus somnus* infection, comprising administering an immunogenic *H. somnus* organism to the cattle, wherein the administered organism possesses characteristics different from those of the wild type virulent organism, the differences comprising the lack of expression of one or more immunoglobulin binding proteins produced by the wild type virulent organism, susceptibility to killing by bovine complement-containing serum, and reduced shedding of endotoxin during growth.

2. The method of claim 1, wherein the administered organism comprises a live vaccine.

3. The method of claim 1, wherein the administered organism comprises a killed vaccine.

4. The method of claim 1, wherein one or more immunoglobulin binding proteins is missing from the administered organism by deletion of one or more genes encoding the one or more immunoglobulin binding proteins from the *H. somnus* genome.

5. The method of claim 4, wherein the administered organism further expresses one or more protective antigens.

6. The method of claim 5, wherein the protective antigen is a 40 kDa *H. somnus* outermembrane protein.

7. The method of claim 1, wherein the administered organism is selected from the group consisting of PTA-600, PTA-601, PTA-602 and PTA-603, deposited with the American Type Culture Collection.

8. The method of claim 5, wherein the administered organism is genetically engineered to express said one or more protective antigens.

9. The method of claim 8, wherein one or more of the protective antigens is from a pathogen other than *H. somnus*.

10. The method of claim 1, wherein an immunoglobulin binding site inactivated in the administered organism is encoded by wild type *H. somnus* gene p120.

11. The method of claim 1, wherein the administered organism is administered as a pharmaceutically acceptable vaccine composition.

* * * * *